(12) United States Patent
van 't Klooster (10) Patent No.: US 7,465,857 B1
(45) Date of Patent: Dec. 16, 2008

(54) GLYPHOSATE TOLERANT PERENNIAL RYEGRASS

(75) Inventor: Gerardus J. M. van 't Klooster, Doornenburg (NL)

(73) Assignee: Barenbrug USA, Inc., Tangent, OR (US)

( * ) Notice: Subject to any disclaimer, the term of this patent is extended or adjusted under 35 U.S.C. 154(b) by 261 days.

(21) Appl. No.: 11/039,403

(22) Filed: Jan. 19, 2005

Related U.S. Application Data (60) Provisional application No. 60/543,354, filed on Feb. 9, 2004.

(51) Int. Cl.
*A01H 5/00* (2006.01)
*A01H 5/10* (2006.01)
*A01H 4/00* (2006.01)
*A01H 1/00* (2006.01)

(52) U.S. Cl. .......... 800/323; 800/260; 800/265; 800/278; 800/279; 800/300; 800/301; 800/302

(58) Field of Classification Search .......... 800/260, 800/265, 278, 279, 300, 301, 302, 320, 323
See application file for complete search history.

*Primary Examiner*—David H Kruse
*Assistant Examiner*—Keith O. Robinson
(74) *Attorney, Agent, or Firm*—Paula A. DeGrandis; Klarquist Sparkman, LLP (57) ABSTRACT

A glyphosate-tolerant perennial ryegrass (*Lolium perenne*) variety, in one example known as experimental code BAR Lp 2703, seed used to produce the grass, and methods of using the grass plant and the seed are provided. This grass is suitable for use in lawns, golf courses, sod, and other turfs, for example where weeds are or may become a problem. Weed control in areas planted with the disclosed grasses can be achieved by direct application of glyphosate herbicides.

40 Claims, 3 Drawing Sheets

GLYPHOSATE TOLERANT PERENNIAL RYEGRASS

CROSS-REFERENCE TO RELATED APPLICATION

This application claims priority to U.S. Provisional Application No. 60/543,354 filed Feb. 9, 2004, herein incorporated by reference in its entirety.

FIELD

This disclosure relates to a perennial ryegrass that is tolerant to glyphosate at levels sufficient to remove grass weed species from various turfs. One example of this grass is known as experimental code BAR Lp 2703.

BACKGROUND

Perennial ryegrasses (*Lolium* species), also called English ryegrass, is a temperate (cool-season) perennial grass that is native to Europe, temperate Asia, and North Africa. It has been widely distributed to other parts of the world, including North and South America, Europe, New Zealand, and Australia. Perennial ryegrass is valued for high yield potential, fast establishment, reduced tillage renovation applications, and use on heavy and waterlogged soils.

Two types of perennial ryegrasses, forage and turf, are most commonly grown. Forage-type perennial ryegrasses are important grasses in forage-livestock systems. High palatability and digestibility make this species highly valued for use in dairy and sheep forage systems. As a result, it often is the preferred forage grass in temperate regions of the world.

Use of perennial ryegrass for turf has increased in recent years with selection of more dense and persistent turf types. It is one of the most versatile of all turfgrass species. For turf, perennial ryegrass is used alone or in combination with other grasses. For the southern region of the U.S., perennial ryegrass's intolerance to high temperature has become an advantage; it is used to overseed dormant Bermuda grass (*Cynodon dactylon*) on Southern lawns and sports fields during the winter months. The perennial ryegrass thins and often dies during hot spring and summer weather, allowing the transition to Bermuda grass turf thus maintaining an active surface suitable for golf and other sports.

Glyphosate (N-(phosphonomethyl) glycine) is the active ingredient in glyphosate herbicides, such as ROUNDUP® brand herbicide produced by Monsanto (St. Louis, Mo.). Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® brand herbicide.

Glyphosate is a broad spectrum herbicide that inhibits the enzyme enolpyruvylshikimate-phosphate synthase (ESPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate, including U.S. Pat. Nos. 4,405,531; 5,118,338; 5,196,044; 5,639,711; 5,652,197; 5,679,621; and 5,750,468.

Little success has been reported in finding natural resistance to glyphosate herbicides in plants. This is beneficial in one respect since it indicates that the likelihood of glyphosate resistant populations of weeds arising is low, but it also means that few naturally resistant desirable plant species are available. As a result, great care must be taken when applying glyphosate herbicides in the vicinity of desirable plants (such as crops, ornamentals, and grass turf). Glyphosate herbicides are highly effective against all grass species and therefore have not been previously known to be applied to control weed growth in turf-type perennial ryegrasses.

SUMMARY

Herein disclosed is a perennial ryegrass variety, which is sufficiently glyphosate tolerant to survive applications of glyphosate herbicides at levels sufficient to kill many common grass weeds that grow in grass plantings. One example of such a glyphosate tolerant perennial ryegrass is termed experimental code BAR Lp 2703. As used herein, a glyphosate-tolerant perennial ryegrass is capable of tolerating application of herbicide at effective rates. Particular examples of "herbicide effective application rates" include, but are not limited to, at least about 3 fluid ounces per acre, at least about 4 fluid ounces per acre, at least about 5 fluid ounces per acre, at least about 9 fluid ounces per acre, at least about 10 fluid ounces per acre, or even at least about 16 fluid ounces per acre of agricultural grade formulations of glyphosate-based herbicides (such as ROUNDUP PRO®, Monsanto, St. Louis, Mo.) (equivalent to application of approximately 0.0105 g/square meter, approximately 0.014 g/square meter, approximately 0.0175 g/square meter, approximately 0.0315 g/square meter, approximately 0.035 g/square meter, and approximately 0.056 g/square meter of the active ingredient, glyphosate in its isopropylamine salt form, respectively).

In one example, the perennial ryegrass variety referred to as experimental code BAR Lp 2703 is tolerant to application of at least about 3 fluid ounces per acre, such as at least about 3.2 fluid ounces per acre, of agricultural grade formulations of glyphosate-based herbicides (equivalent to application of approximately 0.0105 g/square meter and 0.0112 g/square meter of glyphosate, respectively). In another example, BAR Lp 2703 is tolerant to application of at least about 4 fluid ounces per acre, such as at least about 4.8 fluid ounces per acre, of agricultural grade formulations of glyphosate-based herbicides (equivalent to application of approximately 0.014 g/square meter and 0.0168 g/square meter of glyphosate, respectively). In another example, BAR Lp 2703 is tolerant to application of at least about 9 fluid ounces per acre of agricultural grade formulations of glyphosate-based herbicides, such as at least about 9.6 fluid ounces per acre (equivalent to application of approximately 0.0315 g/square meter and 0.0336 g/square meter of glyphosate, respectively). In another example, BAR Lp 2703 is tolerant to application of at least about 16 fluid ounces per acre of agricultural grade formulations of glyphosate-based herbicides (equivalent to application of approximately 0.056 g/square meter of glyphosate). Use of this grass as turf (for example in lawns, on golf courses, in parks, and along roadsides) permits ready control of weeds by application of a glyphosate herbicide.

At least 2500 seeds of the perennial ryegrass variety BAR Lp 2703 have been deposited with the American Type Culture Collection (ATCC, Manassas, Va.; ATCC Deposit No.: PTA-5781). Therefore, these seeds are known and readily available to the public.

In one example, the disclosure provides perennial ryegrass plants that include, and in some examples consist of, or consist essentially of, the morphological and physiological characteristics of the perennial ryegrass known as experimental code BAR Lp 2703, as well as seeds of such plants. In another example, the disclosure provides perennial ryegrass plants having the genotype of BAR Lp 2703. The disclosure also encompasses perennial ryegrass plants produced by crossing BAR Lp 2703 with other grass varieties, as well as seeds of such plants. The present disclosure also provides methods of producing grass seed that include planting seed from BAR Lp 2703 (such as ATCC Deposit No.: PTA-5781) under conditions that result in the germination of the seed, growth of grass plants and setting of progeny seed, and then harvesting the progeny seed.

The disclosure also provides perennial ryegrass plants produced by exposing BAR Lp 2703 to at least 16 fluid ounces per acre of agricultural grade formulations of glyphosate-based herbicides, or greater amounts, such as at least 32, at least 64, or even at least 128 fluid ounces per acre of agricultural grade formulations of glyphosate-based herbicides, and selecting those plants which survive such exposures. These methods can be used to identify perennial ryegrass plants that can tolerate applications of at least 16 fluid ounces per acre of agricultural grade formulations of glyphosate-based herbicides, such as at least 32, at least 64, or even at least 128 fluid ounces per acre of agricultural grade formulations of glyphosate-based herbicides.

A method is provided for producing a glyphosate-tolerant grass plant by crossing a first grass plant with one or more other grass plants to produce progeny grass plants, wherein the first grass plant is a BAR Lp 2703 variety or a glyphosate-tolerant cross derived from an BAR Lp 2703 variety, and then screening the progeny grass plants to select a progeny grass plant that is tolerant to glyphosate. Glyphosate-tolerant grass plants produced by this method are also encompassed by the disclosure.

These and other aspects of the present disclosure will become more apparent from the following description.

BRIEF DESCRIPTION OF THE FIGURES

FIG. 2 is a graph showing Roundup PRO® herbicide damage to BAR Lp 2703 ryegrass.

DETAILED DESCRIPTION OF SEVERAL EMBODIMENTS

The following examples are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a grass plant" includes a plurality of such plants and reference to "the seed" includes reference to one or more seeds and equivalents thereof known to those skilled in the art, and so forth. Similarly, the word "or" is intended to include "and" unless the context clearly indicates otherwise. Hence "comprising A or B" means including A, or B, or A and B.

Unless explained otherwise, all technical and scientific terms used herein have the same meaning as commonly understood to one of ordinary skill in the art to which this disclosure belongs.

EXAMPLE 1

Origin and Breeding History of Perennial Ryegrass Variety Bar Lp 2703

The BAR Lp 2703 turf-type perennial ryegrass (*Lolium perenne*) variety was developed by Barenbrug U.S.A., Inc. as follows. This variety was developed for its tolerance to glyphosate.

In 1983, plants of the varieties Barclay (Plant Variety Protection No. 8300016) and Barrage (Plant Variety Protection No 8900084) were planted in a greenhouse in Wolfheze, The Netherlands for over-wintering. In 1984, a pair cross of the varieties Barclay and Barrage were developed as follows: 15 plants of one variety were crossed with 15 plants of the other parent. For each cross, five stems were harvested. The seed of the 15 mother plants were cleaned and seeded in a greenhouse in the spring of 1985. For each line, 15 plants were planted in the greenhouse and later planted as a polycross in an isolated block. Forage rye was used as isolation plants. Due the dry summer in Wolfheze a replanting was necessary in 1986.

In 1987, F2 seed was harvested from the crossing of each plant. A total of 40 plants were harvested as half sib seed. In 1988, the half sib seed was used in a turf trial with micro plots, 3 replications in Wolfheze. This turf trial was treated with a wear machine to simulate the traffic on the turf. In the spring of 1990, a selection was performed: 15 plants each out of the 5 best families were chosen. These 75 plants were planted as a polycross in an isolated area in Wolfheze and harvested late in the summer of 1990.

In the early spring of 1991, 400 plants were planted on a space plant trial field (30×30 cm) in Lelystad, The Netherlands. This area is known for its high crown rust (*Pucinia coronata*) pressure. In early September 1991, 15 resistant clones were selected, divided to 9 plants, and re-planted on another trial field in Wolfheze. In 1992, just after the heading of all the plants, but before the plants showed flowers, 4 clones were selected on morphological characters and planted as a polycross in an isolated (rye) area. Seed of the plants was harvested in 1992.

From 1993-96, turf trials were conducted in Wolfheze, The Netherlands. The variety showed a good wear tolerance and a good sod density. In 1996, the trials were treated with glyphosate to kill the trials. The normal rate was used (3.5-4 L Roundup PRO®/ha), but after three weeks, three areas in the trial field (6000 plots total) were still green. It was determined that the three green spots were the three replications of the variety, which was termed BAR Lp 2703.

In 1997, a small one replication trial with glyphosate was conducted with 2 split applications of 1 liter Roundup PRO®/ha, and BAR Lp 2703 showed again the tolerance to glyphosate. In 1998, a three-replication trial (plot size was 6 sq. m) with more varieties and different rates of glyphosate showed the same tolerance (Table 1). The mean turf color rating for the BAR LP 2703 variety in this perennial ryegrass turf trial that was seeded in the spring of 1998 (at 16 kg/ha) in Wolfheze was 7.6 in June/July 1998 (9=completely green).

TABLE 1

Results of Roundup® Application

| | | Turf Color After Spraying | | | | |
|---|---|---|---|---|---|---|
| | | 6 Jun. | 8 Jun. | 19 Jun. | 12 Jul. | Average |
| BAR Lp 2793 | EK-2703 | 8 | 7.3 | 7.7 | 7.3 | 7.6 |
| | EK-2720 | 6.3 | 6 | 6.7 | 7.3 | 6.6 |
| | EK-2719 | 6.3 | 6 | 6.3 | 2 | 5.2 |
| | BARDESSA | 5 | 4.7 | 5.3 | 2.3 | 4.3 |
| | BARRAGE | 4.3 | 6 | 4.3 | 1.3 | 4 |
| | B'LOUISE | 4.3 | 4 | 4.7 | 2 | 3.8 |
| | BARLUXE | 4.3 | 3.3 | 3.7 | 1 | 3.1 |
| cv.(variet) | | 10.9 | 17.2 | 6 | 12.6 | 8.6 |
| LSD (.05) | | 1.9 | 3 | 1.1 | 1.6 | 1.4 |

In 1999, a small multiplication of 1000 space plants was performed in Renkum, The Netherlands. About 2% of types rogued out. In 2000, seed of BAR Lp 2703 was harvested.

Seed propagation is limited to three generations of increase from breeder seed: one each of foundation, registered and certified. Breeder seed is stored in environmental controlled long-term storage in Oosterhout, The Netherlands. A breeder seed field was established at West Coast Research Center Farm, Albany Oreg. BAR Lp 2703 is a stable and uniform variety. No off-types or variants have been observed in the reproduction or multiplication of this variety from the breeder seed nursery to the foundation field.

EXAMPLE 2

Seed Deposits

Seeds of the turf-type perennial ryegrass variety referred to herein as experimental code BAR Lp 2703, were deposited with the ATCC (Manassas, Va.) on Jan. 20, 2004 under accession number PTA-5781. The variety is also maintained at, and available from, Barenbrug, U.S.A., Inc., P.O. Box 239, Tangent, Oreg. 97389.

EXAMPLE 3

Turf Characteristics for BAR Lp 2703

The turf characteristics shown in Tables 2 and 3 were observed for BAR Lp 2703 plants at various stages of growth after establishment grown in turf plots in Wolfheze, The Netherlands. In some examples, the BAR Lp 2703 variety is additionally characterized by the following results from various trials. However, variations on these measurements may be observed for plants of differing ages, grown in other locations, or under different prevailing weather conditions.

The mean turf quality rating for the BAR Lp 2703 variety in a perennial ryegrass turf trial that was seeded in 1993 in Wolfheze, The Netherlands (plot size 1.25 sq. m; 3 replications), and subjected to home lawn mowing heights, was 5.1 at 2 cm mowing height, 5.2 at 7 cm mowing height, and 5.1 at winter-fusarium (9=best) (results shown in Table 2).

TABLE 2

Turf Quality of Perennial Ryegrass Varieties (Home Lawn, Low Mowing Height)

| | A | B | C |
|---|---|---|---|
| Bardessa | 5.7 | 5.7 | 5.3 |
| ELKA | 5.4 | 5.9 | 5.6 |
| EK-2703 | 5.1 | 5.2 | 5.1 |
| BARLUXE | 4.8 | 3.7 | 5.3 |
| BARLOW | 4.8 | 4.1 | 4.4 |
| cv.(variet) | 3 | 4.9 | 8.4 |
| LSD (.05) | 0.5 | 0.7 | 1.2 |

A = Average of 10 Turf Quality Obserations at 2 cm mowing height (Sep. 10, 1993; Oct. 26, 1993; Jun. 29, 1994; Jun. 29, 1994; Aug. 18, 1994; Nov. 8, 1994; Jan. 19, 1995; Feb. 24, 1995; May 15, 1995; Jun. 6, 1995)
B = Average of 4 turf quality observations at 7 mm mowing height ( Jun. 29, 1994; Aug. 18, 1994, May 15, 1995, Jun. 6, 1995)
C = Winter-fusarium Jan. 7, 1994

The mean turf quality rating for the BAR Lp 2703 variety in a perennial ryegrass turf trial that was seeded in 1993 in Wolfheze, The Netherlands (plot size 1.25 sq. m; 3 replications), and subjected to wear conditions experienced in a sports field, was 5.5 at establishment, 6.5 three-weeks after establishment, 6.7 after one month of wear, 5.3 after 1.5 years of wear, 4.5 after drought, and 5.7 at winter (9=best) (results shown in Table 3).

TABLE 3

Turf Perennial Ryegrass trial (Sports Field Management, Mowing Height 2 cm)

| Variety | A | B | C | D | E | F |
|---|---|---|---|---|---|---|
| Bardessa | 4.3 | 4.6 | 5.7 | 5.5 | 5.5 | 4.8 |
| EK-2703 | 5.5 | 6.5 | 6.7 | 5.3 | 4.5 | 5.7 |
| Barsportivo | 4.6 | 5.6 | 5.7 | 5.2 | 5 | 5.3 |
| BARRAGE | 4.9 | 5 | 5.3 | 4.7 | 5.3 | 4.8 |
| SURPRISE | 4 | 4.2 | 5.4 | 4.6 | 5.2 | 4.6 |
| FLAIR | 4.7 | 3.8 | 5.3 | 4.6 | 5 | 4.5 |
| Sabor | 5.5 | 4.1 | 3.9 | 4.4 | 3.7 | 3.4 |
| cv. (variet) | 6.4 | 6.5 | 8.2 | 3.2 | 9.9 | 5.2 |
| LSD (.05) | 1 | 1.1 | 1.4 | 0.5 | 1.5 | 0.7 |

A = Establishment Jul. 21, 1993.
B = Turf Quality Aug. 10, 1993
C = Turf Quality after wear Sep. 21, 1993
D = Average of 8 Turf Quality observations after wear: Sep. 21, 1993; Oct. 5, 1993; Nov. 8, 1993; Jan. 3, 1994; May 10, 1994; Nov. 8, 1994; Feb. 24, 1995; Jun. 13, 1995
E = Average of 2 Turf Quality observations after drought Jul. 22, 1994; Jul. 7, 1995
F = Average of 3 winter Turf quality observation Dec. 6, 1993; Jan. 20, 1995; Mar. 25, 1996

EXAMPLE 4

Morphological Characteristics

The morphological characteristics shown in Tables 4a and 4b were observed for BAR Lp 2703 plants and other turf perennial ryegrass varieties listed. Grass plants were established from seed in a greenhouse on Oct. 9, 2003 and later transplanted to field on Dec. 3, 2003 at Barenbrug U.S.A. West Coast Research Center, Albany, Oreg. The plants were arranged in randomized complete block design with 3 replications and 20 plants per replication. Plants were established at a spacing of 2×2 feet. Each of the twenty plants was established in a 4×5 plant formation with a plot. Morphological measurements were obtained between Apr. 30, 2003 and Jul. 31, 2003. Variations on these measurements may be observed for plants of differing ages, grown in other locations, or under different prevailing weather conditions.

TABLE 4a

Plant Morphological Measurements in Perennial Ryegrass Varieties

| Variety | Tiller Leaf Width (mm) | Tiller Leaf Length (cm) | 1st Internode Length (cm) | Peduncle Length (cm) | Panicle Height (cm) | Plant Height (cm) | Flag Leaf Height (cm) |
|---|---|---|---|---|---|---|---|
| Barclay | 4.7 a | 17.8 a | 8.0 d | 8.0 e | 40.3 a | 64.4 b | 30.1 bc |
| Pleo | 4.2 a | 17.5 a | 10.0 bcd | 11.0 cde | 46.8 a | 67.3 b | 34.7 b |
| Norlea | 4.1 ab | 18.8 a | 13.7 a | 9.3 de | 60.5 a | 87.7 a | 50.3 a |
| Peak | 3.4 bc | 13.0 bc | 12.0 ab | 15.6 ab | 51.9 a | 69.6 b | 34.8 b |
| Barlennium | 3.2 c | 12.2 bc | 10.7 bc | 12.9 bcd | 45.2 a | 62.1 b | 30.6 bc |
| Linn | 3.2 c | 14.0 b | 13.8 a | 15.0 abc | 49.9 a | 67.8 b | 33.1 b |
| 00-Lp-1b | 2.9 c | 12.1 bc | 9.8 bcd | 12.7 bcd | 45.1 a | 61.6 b | 31.5 bc |
| Pinnacle | 2.9 c | 12.7 bc | 11.4 ab | 12.4 bcd | 45.2 a | 63.0 b | 30.3 bc |
| Premier II | 2.8 c | 10.8 c | 11.1 b | 10.9 cde | 44.9 a | 62.1 b | 32.4 bc |
| Pinnacle II | 2.8 c | 12.0 bc | 10.0 bcd | 11.2 cde | 44.7 a | 61.0 b | 32.1 bc |
| 00-Lp-1 | 2.8 c | 12.4 bc | 10.5 bcd | 12.7 bcd | 47.2 a | 64.8 b | 34.1 b |
| Lp 2703 | 2.6 c | 10.2 c | 9.7 bcd | 13.6 bcd | 48.0 | 67.2 b | 32.9 b |
| RAKR 85 | 2.6 c | 13.0 bc | 8.4 cd | 17.6 a | 42.3 | 59.6 b | 24.0 c |
| LSD (P = .05) | 0.71 | 2.45 | 2.37 | 3.66 | ns | 13.04 | 7.39 |
| CV | 13.0 | 10.69 | 13.14 | 17.33 | 13.02 | 11.73 | 13.23 |

Means followed by same letter do not significantly differ (P = .05, Duncan's New MRT)

TABLE 4b

Plant Morphological Measurements in Perennial Ryegrass Varieties

| Variety | Flag Leaf Height (cm) | Flag Leaf Length (cm) | Flag Leaf Width (mm) | Panicle Length (cm) | Heading Day (Julian) | Anthesis Day (Julian) |
|---|---|---|---|---|---|---|
| Barclay | 30.1 bc | 17.9 a | 5.6 a | 22.6 b | 165.5 a | 176.8 a |
| Pleo | 34.7 b | 16.5 a | 5.0 ab | 20.1 c | 150.8 b | 170.1 b |
| Norlea | 50.3 a | 18.8 a | 4.5 bc | 26.3 a | 146.5 b | 169.8 bc |
| Peak | 34.8 b | 11.3 b | 3.9 cd | 17.4 de | 127.6 f | 158.6 fg |
| Barlennium | 30.6 bc | 11.0 b | 3.9 cd | 16.5 de | 135.5 cde | 167.2 bcd |
| Linn | 33.1 b | 11.9 b | 3.8 cde | 17.5 de | 119.3 g | 149.8 h |
| 00-Lp-1b | 31.5 bc | 11.0 b | 3.4 de | 16.1 de | 135.0 de | 165.8 bcd |
| Pinnacle | 30.3 bc | 10.3 b | 3.3 de | 16.2 de | 128.6 f | 160.4 ef |
| Premier II | 32.4 bc | 10.5 b | 3.1 de | 16.1 de | 135.6 cde | 165.1 d |
| Pinnacle II | 32.1 bc | 11.2 b | 3.3 de | 15.3 e | 138.5 cd | 166.8 bcd |
| 00-Lp-1 | 34.1 b | 12.1 b | 3.4 de | 17.0 de | 136.3 cd | 164.5 de |
| Lp 2703 | 32.9 b | 9.6 b | 3.0 e | 18.0 cd | 140.2 c | 165.4 cd |
| RAKR 85 | 24.0 c | 11.5 b | 3.0 e | 17.0 de | 130.5 ef | 155.4 g |
| LSD (P = .05) | 7.39 | 2.37 | 0.76 | 2.25 | 4.69 | 4.15 |
| CV | 13.23 | 11.19 | 11.88 | 7.35 | 2.02 | 1.5 |

Means followed by same letter do not significantly differ (P = .05, Duncan's New MRT)

EXAMPLE 5

Herbicide Treatments

Figure 1:
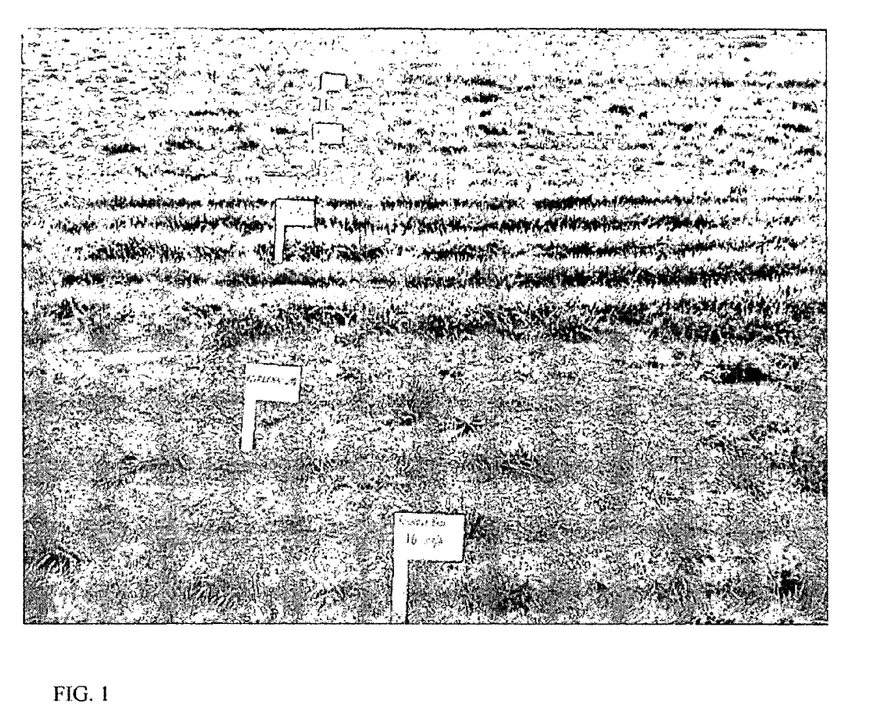
FIG. 1 is a digital image comparing the growth of BAR Lp 2703 and other perennial ryegrass varieties (Barlennium, Pirouette, and Peak) in the presence of 16 fl oz/acre Roundup PRO® herbicide.

This example provides methods and results of field trials in which the glyphosate resistance characteristics of BAR Lp 2703 were examined and compared with other standard perennial ryegrass varieties (Peak, Pirouette and Barlennium). The four turf perennial ryegrass varieties were sowed at 7 inch row spacing on Oct. 17, 2002 at Barenbrug U.S.A. West Coast Research Center, Albany, Oreg., and rated between February 2003 and May 2003 (FIG. 1). The trial was established as a Strip-Plot Design with four replications. Perennial ryegrass varieties were sowed in separate strips (5 feet wide), North-South and herbicide treatments (8 feet wide) applied perpendicular to grass strips in East-West directions.

Because perennial ryegrass growth was very slow through the winter months in Oregon, the grasses were not mowed before the first herbicide treatments were applied. Herbicide treatments were applied with a handheld broom, with $CO_2$ propulsion at 22 gallons per acre (gpa). The first herbicide applications were made on Feb. 8, 2003 (air temperature 50° F., soil temperature at 2 inch was 40° F. and at 4 inch was 38° F., perennial ryegrass: 4.5 leaf and 2 tillers, 2 inches in height, *Poa annua*: 4.5 leaf, 2 tillers and 1 inch tall).

The second herbicide application was made on May 2, 2003 (air temperature: 60° F., soil temperature at 2 inch 65° F. and at 4 inch was 60° F., perennial ryegrass: 3.5 inch tall (mowed 10 days prior) thick 4 inch rows, *Poa annua*: flowering, seed heads formed, also mowed 10 days prior).

The following herbicides were used: Roundup PRO® (glyphosate, Monsanto, St. Louis, Mo.) ethofumesate (Nortron®, Bayer CropScience LP, Research Triangle Park, N.C.) and Gramaxone® Max (Paraquat, Syngenta Corporation). Roundup PRO® was used since it is registered for use in turf. Roundup PRO® is also registered for use in dormant turfgrass for control of winter annual weeds.

Effects of herbicide treatments on different perennial grass varieties and *Poa annua* was visually evaluated on the scale of 0-100. When no plant injury from herbicide treatment was observed on the grass, it was given a rating of zero, and on the other end if all the plants were killed, it was given a rating of 100% injury. The data was statistically analyzed with ANOVA after squareroot transformation.

The ability of Roundup PRO® to control the weed *Poa annua* (annual bluegrass), was determined using the methods described above. As shown in Table 4, Gramaxone Max® provided immediate control of *Poa annua* soon after herbicide application. By March 1, all Roundup PRO® treatments and Gramazone® Max treatments were showing injury to *Poa annua*. However, *Poa annua* control from Nortron® was very low. Three weeks after Roundup PRO® application, even the low rates of 4.8 fluid ounces per acre (fl oz/A) provided statistically similar *Poa annua* control to the highest rate of 16 fl oz/A. A similar observation was made at 11 weeks (April 29) after Roundup PRO® application. There was no difference between *Poa* annua control provided by application rates of 4.8, 8.0, 9.6, and 16 fl oz/A of Roundup PRO®.

The second application of Roundup PRO® in the split application treatments was made on May 2, 2003. As shown in Table 5 (May 29), the split treatment of 8 fl oz/A was better than split treatment of 4.8 fl oz/A.

TABLE 5

*Poa annua* control by different herbicide treatments in perennial ryegrass

| Herbicide | Amount of Herbicide | Date of Application | Feb 14# | March 1# | April 29# | May 29# |
|---|---|---|---|---|---|---|
| Roundup Pro | 3.2 fl oz/A | Feb 8 | 0 c | 50 c | 65 d | |
| Roundup Pro | 4.8 fl oz/A | Feb 8 | 0 c | 68 bc | 89 abc | |
| Roundup Pro | 9.6 fl oz/A | Feb 8 | 0 c | 83 ab | 92 abc | |
| Roundup Pro | 16 fl oz/A | Feb 8 | 0 c | 80 ab | 100 a | |
| Nortron | 3 pints/A | Feb 8 | 10 b | 18 d | 98 ab | |
| Gramaxone Max* | 2 pints/A | Feb 8 | 81 a | 100 a | 100 a | |
| Roundup Pro | 4.8/4.8 fl oz/A | Feb 8/May 2 | 0 c | 48 c | 82 c | 80 b |
| Roundup Pro | 8/8 fl oz/A | Feb 8/May 2 | 0 c | 78 ab | 86 bc | 98 a |
| Roundup Pro | 32 fl oz/A | May 2 | 0 c | | | 100 a |
| Untreated | | | 0 c | | | 0 c |

*Gramaxone applied with 0.25% v/v non-ionic surfactant (No Foam A). #Numbers followed by the same letter are not statistically different (p = 0.05)

The amount of herbicide that provided adequate control of annual bluegrass (*Poa annua*) but did not injure perennial ryegrass, was also determined.

Increasing the amount of Roundup PRO® applied increased the injury to all perennial ryegrass varieties (Tables 6-8). All perennial ryegrass varieties examined exhibited slight tolerance to Roundup PRO®. On March 1 (3 weeks after application), injury to Peak, Pirouette and Barlennium were similar (Table 6). However, injury to BAR Lp 2703 was only about 50% of the other three varieties at all rates except 16 fl oz/A. These results demonstrate that BAR Lp 2703 is tolerant to glyphosate at an early growth stage of perennial ryegrass growth.

TABLE 6

Perennial ryegrass injury (March 1) from different herbicide treatments.

| Herbicide | Amount of Herbicide | Date of Application | Peak | BAR Lp 2703 | Pirouette | Barlennium |
|---|---|---|---|---|---|---|
| Roundup Pro | 3.2 FL OZ/A | Feb 8 | 13 | 8 | 13 | 10 |
| Roundup Pro | 4.8 FL OZ/A | Feb 8 | 29 | 18 | 26 | 23 |
| Roundup Pro | 9.6 FL OZ/A | Feb 8 | 58 | 38 | 54 | 56 |
| Roundup Pro | 16 FL OZ/A | Feb 8 | 79 | 63 | 74 | 75 |
| Nortron | 3 PT/A | Feb 8 | 0 | 3 | 0 | 0 |
| Gramaxone Max* | 2 PT/A | Feb 8 | 100 | 100 | 100 | 100 |
| Roundup Pro | 4.8/4.8 FL OZ/A | Feb 8/May 2 | 34 | 16 | 29 | 26 |
| Roundup Pro | 8/8 FL OZ/A | Feb 8/May 2 | 49 | 28 | 50 | 50 |
| Roundup Pro | 32 FL OZ/A | May 2 | — | — | — | — |
| Untreated | | | 0 | 0 | 0 | 0 |

*Gramaxone applied with 0.25% v/v non-ionic surfactant (No Foam A). Least significant difference (0.05) between varieties × herbicide treatments = 10. The interaction was not statistically significant Eleven weeks after Roundup PRO® application, Peak, Pirouette and Barlennium still had similar injury as shown 8 weeks prior (Table 7). In contrast, BAR Lp 2703 recovered considerably. Even at 16 fl oz/A, only 30% injury was observed.

TABLE 7

Perennial ryegrass injury (April 29) from different herbicide treatments.

| Herbicide | Amount of Herbicide | Date of Application | Peak | BAR Lp 2703 | Pirouette | Barlennium |
|---|---|---|---|---|---|---|
| Roundup Pro | 3.2 FL OZ/A | Feb 8 | 3 | 1 | 6 | 5 |
| Roundup Pro | 4.8 FL OZ/A | Feb 8 | 14 | 4 | 21 | 19 |
| Roundup Pro | 9.6 FL OZ/A | Feb 8 | 50 | 9 | 54 | 70 |
| Roundup Pro | 16 FL OZ/A | Feb 8 | 83 | 30 | 90 | 90 |
| Nortron | 3 PT/A | Feb 8 | 3 | 0 | 5 | 3 |
| Gramaxone Max* | 2 PT/A | Feb 8 | 97 | 93 | 98 | 96 |
| Roundup Pro | 4.8/4.8 FL OZ/A | Feb 8/May 2 | 8 | 3 | 9 | 10 |
| Roundup Pro | 8/8 FL OZ/A | Feb 8/May 2 | 28 | 9 | 29 | 26 |
| Roundup Pro | 32 FL OZ/A | May 2 | — | — | — | — |
| Untreated Check | | | 0 | 0 | 0 | 0 |

*Gramaxone applied with 0.25% v/v non-ionic surfactant (No Foam A). Least significant difference (0.05) between varieties × herbicide treatments = 14. The interaction was statistically significant.

The second application of Roundup PRO® in the split treatments was made on May 2, 2002. Evaluations 3.5 weeks after application showed significant injury to all perennial ryegrass varieties (Table 8). However, at lower rates (4.8 and 8 fl oz/A) BAR Lp 2703 had significantly less injury compared to Peak, Pirouette, and Barlennium.

TABLE 8

Perennial ryegrass injury (May 31) from different herbicide treatments.

| Herbicide | Amount of Herbicide | Date of Application | Peak | BAR Lp 2703 | Pirouette | Barlennium |
|---|---|---|---|---|---|---|
| Roundup Pro | 3.2 FL OZ/A | Feb 8 | — | — | — | — |
| Roundup Pro | 4.8 FL OZ/A | Feb 8 | — | — | — | — |
| Roundup Pro | 9.6 FL OZ/A | Feb 8 | — | — | — | — |
| Roundup Pro | 16 FL OZ/A | Feb 8 | — | — | — | — |
| Nortron | 3 PT/A | Feb 8 | — | — | — | — |
| Gramaxone Max* | 2 PT/A | Feb 8 | — | — | — | — |
| Roundup Pro | 4.8/4.8 FL OZ/A | Feb 8/May 2 | 21 | 5 | 23 | 30 |
| Roundup Pro | 8/8 FL OZ/A | Feb 8/May 2 | 89 | 20 | 91 | 83 |
| Roundup Pro | 32 FL OZ/A | May 2 | 99 | 81 | 98 | 99 |
| Untreated Check | | | 0 | 0 | 0 | 0 |

Gramaxone applied with 0.25% v/v non-ionic surfactant (No Foam A). Least significant difference (0.05) between varieties × herbicide treatments = 7. The interaction was statistically significant.

Tolerance of BAR Lp 2703 to Roundup PRO® application is illustrated in Table 9. As shown in Table 9, BAR Lp 2703 only shows 50% injury compared to other perennial ryegrass varieties when averaged over all application rates of Roundup PRO®. There was no difference between the means of perennial ryegrass injury ratings averaged over all Roundup PRO® treatments (Table 9) versus averaged over all herbicide treatments.

TABLE 9

Perennial ryegrass injury average over all Roundup PRO® treatments

| | Date of Evaluation | | |
|---|---|---|---|
| | Mar. 1, 2003 | Apr. 29, 2003 | May 31, 2003 |
| Peak | 45 | 35 | 52 |
| BAR Lp 2703 | 34 | 19 | 27 |
| Pirouette | 43 | 39 | 53 |
| Barlennium | 43 | 40 | 53 |
| LSD (0.05) | 4 | 5 | 2 |

In summary, Roundup PRO® application rates of 4.8, 8.0, and 9.6 fl oz/A provided fair to good control of *Poa annua* and had minimal injury to perennial ryegrass BAR Lp 2703. The data demonstrate that BAR Lp 2703 grass plants are tolerant to glyphosate herbicide applied at levels or frequency, or both, sufficient to remove weed species, for example from lawns, pasture, golf courses, sod, and turf.

The data demonstrate that BAR Lp 2703 grass plants are tolerant to glyphosate herbicide applied at levels or frequency, or both, sufficient to remove weed species, for example from lawns, pasture, golf courses, sod, and turf. In particular examples, the phrase "a glyphosate tolerant grass plant" is a grass plant that will survive application of agricultural formulations of glyphosate herbicide (containing 41% w/v glyphosate) at levels equivalent of up to about 16 fluid ounces per acre, corresponding to at least about 0.056 g per square meter of active ingredient glyphosate. This level of glyphosate is sufficient to kill some common grass weeds.

At the application rate of 16 fluid ounces per acre of glyphosate herbicide (containing 41% w/v glyphosate) and under the field conditions prevailing at the time the field tests were performed on BAR Lp 2703 (February through May 2003 near Albany, Oreg.), only 63% injury was observed. However, more significant deleterious effects may be observed depending on the age of the grass, the time of year and the prevailing weather conditions. For example, it has been observed that the BAR Lp 2703 variety is more sensitive to glyphosate herbicide (containing 41% w/v glyphosate) applications if treated at very early growth stage.

In addition, the BAR Lp 2703 variety tolerates application of a glyphosate herbicide (containing 41% w/v glyphosate) during an early growth stage (4.5 leaf and 2 tillers, 2 inches in height). BAR Lp 2703 can tolerate additional applications of about at least 4 fluid ounces per acre of glyphosate herbicide the following spring or fall after seeding, where necessary to remove weeds that are difficult to control. When re-applying glyphosate herbicide, the sensitivity of the BAR Lp 2703 variety to ambient temperature, time of year, and age of the grass can be considered.

Higher levels of glyphosate herbicide can be applied to BAR Lp 2703 plants if necessary to eradicate particularly recalcitrant weed species. As shown in the Tables above, BAR Lp 2703 can tolerate application of up to about 16 fluid ounces per acre of agricultural formulations of glyphosate herbicide (equivalent to about 0.056 g per square meter of active ingredient glyphosate) depending on the time of year, age of the plants and environmental conditions. At this level of glyphosate application, 60% injury can be observed, but the grass plants not killed subsequently make a complete recovery.

EXAMPLE 6

Glyphosate Tolerance

This example provides methods and results of field trials in which the glyphosate tolerance characteristics of BAR Lp 2703 were examined and compared with Peak perennial ryegrass in Florence, S.C.

Peak and LP2703 perennial ryegrasses were overseeded at 350 lb/acre on dormant Bermuda grass base on Oct. 7, 2003. Turf quality was rated 7 times between Nov. 10, 2003 and Mar. 2, 2004. Turf quality fluctuated between 6.0 and 7.5 with changes in weather and fertilization (rated on a scale of 1-9 with 1=bare soil and 9=perfect turf).

Experimental treatments were 0, 3, 5, 6, 8, 10, and 16 ounces Roundup PROS per acre. One application of each treatment was applied on Mar. 12, 2004 to plots 3 feet wide by 6 feet long. The 3 and 6 oz/acre treatments were applied a second time on Mar. 28, 2004. There were two replications of each treatment applied to each cultivar. Applications were made in 2 gallons of water per 1000 square feet with a $CO_2$-charged backpack sprayer.

Turf damage was rated on a scale of 0-9 with 0=no damage and 9=complete damage 7, 14, and 21 days after the first spray. Damage was not evident prior to 7 days.

All Roundup PRO® application rates produced some turf damage on BAR Lp 2703, 7 days after the first application (FIG. 2). However, turf damage was low (<1.0) at rates of 3 and 5 oz./acre, with increasing damage at higher rates. In addition, the amount of damage decreased with time for all rates except 16 oz/acre, where damage increased to more than 4.0 at 20 days after the first spray. Greater damage with the second spray of 3 and 6 oz/acre was not evident 4 days after the second application. Wilting, reduced growth, and yellowing of some turf characterized turf damage.

Figure 3:
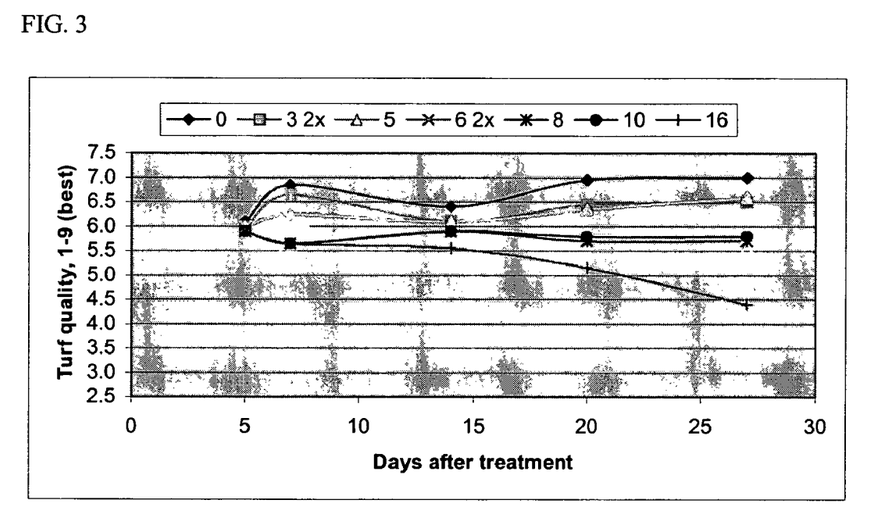
FIG. 3 is a graph showing turf quality of BAR Lp 2703 following application of Roundup PRO® herbicide.

The turf quality of BAR Lp 2703 generally reflected damage ratings (FIG. 3). Lower rates of Roundup PRO® (3 and 5 oz/acre) had turf quality approaching that of the untreated turf. The turf quality of rates above 5 oz/acre of Roundup PRO® were below 6 and did not improve or decreased with time after the first spray.

Figure 4:
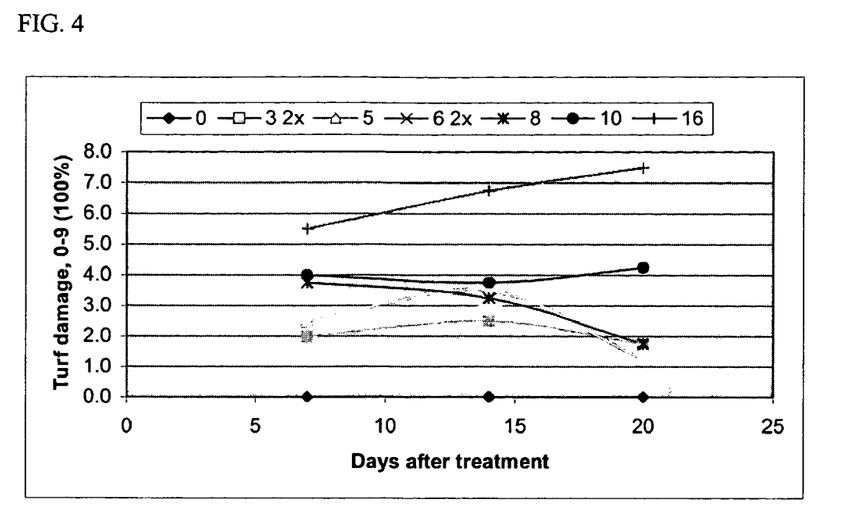
FIG. 4 is a graph showing Roundup PRO® herbicide damage to Peak ryegrass.

The observed turf damage on the Peak cultivar from Roundup PRO® was about two times greater than damage on BAR Lp 2703. Single applications of 5 and 8 oz/acre showed a reduction in turf damage over 27 days, but higher rates and application of 3 and 6 oz/acre rate sprayed twice showed greater damage over time.

Figure 5:
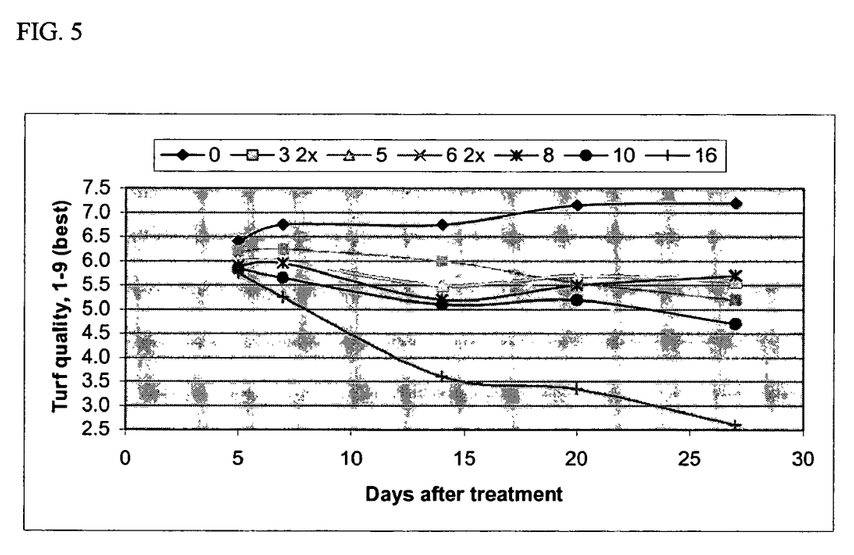
FIG. 5 is a graph showing turf quality of Peak ryegrass following application of Roundup PRO® herbicide.

Turf quality of Peak at all rates of Roundup PRO® was below 6.0 from 5 days after the first spray through 20 days. Although 3 oz/acre Roundup PRO® initially produced acceptable turf quality (within 1 week of the first spray), subsequently, turf quality remained below 6.0 for this application rate as well.

A summary of the turf quality ratings (on a scale from 1-9 with 1=bare soil and 9=perfect turf) is provided in Table 10. The ratings shown in Table 10 were obtained 40 days after the first application of glyphosate (24 days after $2^{nd}$ application).

TABLE 10

| | Turf quality ratings | |
|---|---|---|
| Glyphosate (oz/acre) | Bar Lp 2703 | Peak |
| 0 | 7.5 | 7.6 |
| 3 twice | 6.4 | 5.4 |
| 5 | 7.3 | 6.8 |
| 6 twice | 5.8 | 2.5 |
| 8 | 7.8 | 7.7 |
| 10 | 8.0 | 7.0 |
| 16 | 6.5 | 5.9 |

EXAMPLE 7

Production of Glyphosate-Tolerant Grasses

BAR Lp 2703 can be grown under normal conditions for growing turf-type perennial ryegrasses, and bulk seed for large-scale planting can be obtained by methods known in certified seed production. For example, bulk seed can be produced by planting BAR Lp 2703 variety seeds obtained from ATCC (Accession Number PTA-5781) or Barenbrug U.S.A., Inc., allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, etc. BAR Lp 2703 variety seeds deposited with ATCC are breeder seeds; propagation of plants from these seeds can be performed under the conditions specified in the 1998 Oregon Certified Seed Handbook, published by Oregon State University Extension Service, Corvallis, Oreg. 97331.

BAR Lp 2703 variety can also be asexually reproduced via vegetative propagules, such as sprigs, plugs, and sod.

To confirm maintenance of the glyphosate-tolerance characteristic, a glyphosate herbicide (containing 41% w/v active ingredient glyphosate) can be applied to the plants at the equivalent of at least about 3 fluid ounces per acre, for example at least about 4 fluid ounces per acre, at least about 5 fluid ounces per acre, at least about 9 fluid ounces per acre, at least about 10 fluid ounces per acre, for example up to about 16 fluid ounces per acre.

EXAMPLE 8

Exemplary Uses of the Glyphosate Tolerant Perennial Ryegrasses

The perennial ryegrass variety BAR Lp 2703 can be used in the same way as other perennial ryegrass varieties. However, the tolerance to glyphosate herbicides affords BAR Lp 2703 particular advantages over other varieties. For example, with current commercially available varieties of turf-type perennial ryegrass grasses, the preparation of a lawn that is to be made by seeding requires extensive preparation of the soil to remove weeds that may be present, often including soil fumigation. With BAR Lp 2703, such preparation can be avoided since some weeds that begin to grow in the new lawn are readily removed by application of a glyphosate herbicide. With BAR Lp 2703, glyphosate herbicides can also be used to remove many of the most troublesome lawn weeds such as crabgrass (*Digitaria sanguinalis*), annual bluegrass (*Poa annua*), rattail fescue (*Vulpia myuros*) and annual ryegrass (*Lolium multiforum*). Thus, BAR Lp 2703 is especially marketable and therefore useful.

EXAMPLE 9

Introducing Traits of Bar Lp 2703 into Other Grass Varieties

The morphological and physiological characteristics of the BAR Lp 2703 variety of perennial ryegrass, including the glyphosate tolerance trait, can be introduced into other grass varieties by conventional breeding techniques. For example, the BAR Lp 2703 variety can be grown in pollination proximity to another variety of perennial ryegrass, allowing cross-pollination to occur between the BAR Lp 2703 variety and the other variety, and then harvesting the hybrid seeds. Plants grown from these hybrid seeds can then be tested for the maintenance of the molecular characteristics described above for the BAR Lp 2703 variety, or the plants can simply be observed to see if they display the same growth characteristics described in the above tables.

For example, plants grown from these hybrid seeds can be tested for glyphosate tolerance by application of glyphosate herbicide at various levels. In this way, the glyphosate tolerance characteristic can be combined with other desirable plant characteristics. Thus, the provision of BAR Lp 2703 enables the production of progeny plants of BAR Lp 2703 having the glyphosate tolerance characteristic. "Progeny plants" of BAR Lp 2703 are any plants that are the offspring of a cross between BAR Lp 2703 and any other plant or plants. Progeny plants also include successive generations of the offspring, for example those selected for glyphosate tolerance using the methods described herein. First-generation progeny plants may retain the glyphosate tolerance characteristic of the BAR Lp 2703 parent. However, if a first-generation progeny plant does not retain the desired level of glyphosate tolerance observed with BAR Lp 2703, subsequent generations of offspring can be recycled for glyphosate tolerance which have at least the same resistance characteristics of BAR Lp 2703 described herein, such capable of tolerating application of at least about 3 fluid ounces per acre, for example at least about 4 fluid ounces per acre, at least about 5 fluid ounces per acre, at least about 9 fluid ounces per acre, at least about 10 fluid ounces per acre, for example up to about 16 fluid ounces per acre of a glyphosate herbicide (containing 41% w/v active ingredient glyphosate). In one example, subsequent generations of offspring can have a glyphosate tolerance that exceeds that of BAR Lp 2703, for example capable of tolerating application of at least about 3 fluid ounces per acre, for example at least about 4 fluid ounces per acre, at least about 5 fluid ounces per acre, at least about 9 fluid ounces per acre, at least about 10 fluid ounces per acre, for example up to about 16 fluid ounces per acre of a glyphosate herbicide (containing 41% w/v active ingredient glyphosate).

In addition, BAR Lp 2703 can be used as transformation targets for the production of transgenic grasses. In certain examples, the present disclosure contemplates the transformation of cells derived from the BAR Lp 2703 variety with at least one transgene. Transgenes that can be used, include, but are not limited to, transgenes that confer resistance to herbicides, insect, disease (viral, bacterial, fungal, nematode) or drought resistance, standability, prolificacy, salt damage resistance, and quality. Examples of such genes and methods of transforming plants are described in U.S. Pat. No. 6,025,545 to Lundquist et al. and Jain and Jain (*Indian J. Exp. Biol.* 38:6-17, 2000) herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims.

What is claimed is:

1. A perennial ryegrass plant, comprising all of the morphological and physiological properties of a grass plant grown from the seed deposited under American Type Culture Collection (ATCC) No: PTA-5781.

2. A sod, comprising the perennial ryegrass plant of claim 1.

3. A method of using the perennial ryegrass plant of claim 1, comprising planting the perennial ryegrass plant of claim 1 in a turf.

4. A method of using the perennial ryegrass plant of claim 1, comprising planting the perennial ryegrass plant of claim 1 in a golf course fairway, golf course rough, lawn, or athletic field.

5. A seed of the perennial ryegrass plant of claim 1.

6. A grass seed mixture, comprising the seed of claim 5.

7. A vegetative sprig or clone of the perennial ryegrass plant of claim 1.

8. A method of making a transformed grass plant comprising transforming the perennial ryegrass plant of claim 1 with at least one transgene.

9. A perennial ryegrass plant made by the method of claim 8, wherein the at least one transgene confers upon the perennial ryegrass plant resistance to a bacterial disease, viral disease, fungal disease, nematode, or insect.

10. A perennial ryegrass plant made by the method of claim 8, wherein the at least one transgene confers upon the perennial ryegrass plant drought tolerance or salt tolerance.

11. A seed resulting from crossing the perennial ryegrass plant of claim 1 with a second grass plant.

12. A grass plant grown from the seed of claim 11.

13. A sod, comprising the grass plant of claim 12.

14. A method of using the grass plant of claim 12, comprising planting the grass plant of claim 12 in a turf.

15. A method of using the grass plant of claim 12, comprising planting the grass plant claim 12 in a golf course fairway, golf course rough, lawn, or athletic field.

16. The seed of claim 11, wherein the second grass plant is a perennial ryegrass plant.

17. A method of producing grass seed, comprising
planting the seed of claim 5 under conditions that result in the germination of the seed, growth of grass plants and setting of progeny seed; and
harvesting the progeny seed.

18. A method of producing a glyphosate-tolerant grass plant, comprising:
crossing a first grass plant with at least one other grass plant to produce progeny grass plants, wherein the first grass plant is the perennial ryegrass plant of claim 1;
screening the progeny grass plants to select a progeny grass plant that is tolerant to glyphosate.

19. A glyphosate-tolerant grass plant produced by the method of claim 18.

20. A sod comprising the glyphosate-tolerant grass plant of claim 19.

21. A method of using the perennial ryegrass plant of claim 19, comprising planting the perennial ryegrass plant of claim 19 in a turf.

22. A vegetative sprig or clone of the glyphosate-tolerant grass plant of claim 19.

23. A method of making a transformed grass plant comprising transforming the grass plant of claim 19 with at least one transgene.

24. The method of claim 23, wherein the at least one transgene confers upon the perennial ryegrass plant resistance to a bacterial disease, viral disease, fungal disease, nematode, or insect.

25. The method of claim 23, wherein the at least one transgene confers upon the perennial ryegrass plant drought tolerance or salt tolerance.

26. The glyphosate-tolerant grass plant of claim 19, wherein the grass plant is tolerant to application of up to about 0.0105 g per square meter of glyphosate.

27. The glyphosate-tolerant grass plant of claim 19, wherein the grass plant is tolerant to application of at least about 0.0175 g per square meter of glyphosate.

28. The glyphosate-tolerant grass plant of claim 19, wherein the grass plant is tolerant to application of at least about 0.035 g per square meter of glyphosate.

29. A grass seed deposited as ATCC No: PTA-5781.

30. A method of producing grass seed, comprising
planting the grass seed of claim 29 under conditions that result in the germination of the grass seed, growth of grass plants and setting of progeny seed; and
harvesting the progeny seed.

31. A grass seed produced by the method of claim 30.

32. A mixture of grass seed comprising the grass seed of claim 31.

33. A sod, comprising a grass plant germinated from the seed of claim 31.

34. A method of using the perennial ryegrass plant of claim 31, comprising planting the grass plant of claim 31 in a turf, comprising a grass plant germinated from the seed of claim 31.

35. A grass plant germinated from the seed of claim 31.

36. A method of making a transformed grass plant comprising transforming the grass plant of claim 35 with a transgene that confers upon the grass plant resistance to a bacterial disease, viral disease, fungal disease, nematode, or insect.

37. A method of making a transformed grass plant comprising transforming the grass plant of claim 35 with a transgene that confers upon the grass plant drought tolerance or salt tolerance.

38. A method of producing a glyphosate-tolerant grass plant, comprising:
exposing the perennial ryegrass plant of claim 1 to at least at least about 0.056 g per square meter of glyphosate, thereby generating exposed grass plants;
selecting exposed grass plants that are tolerant to the glyphosate.

39. The method of claim 38, wherein the perennial ryegrass plant is exposed to at least at least about 0.112 g per square meter of glyphosate.

40. The method of claim 38, wherein the perennial ryegrass plant is exposed to at least at least about 0.224 g per square meter of glyphosate.

* * * * *